US00PP28328P3

(12) United States Plant Patent
Ammerlaan

(10) Patent No.: US PP28,328 P3
(45) Date of Patent: Aug. 22, 2017

(54) ***ALOE* PLANT NAMED 'OVALJAWS'**

(50) Latin Name: ***Aloe melanacantha* A. Berger**
Varietal Denomination: Ovaljaws

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 70 days.

(21) Appl. No.: 14/757,065

(22) Filed: Nov. 13, 2015

(65) Prior Publication Data

US 2016/0183439 P1 Jun. 23, 2016

(30) Foreign Application Priority Data

Dec. 18, 2014 (QZ) ..... PBR 2014/3484

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Samuel R. McCoy, Jr.

(57) ABSTRACT

A new and distinct *Aloe* cultivar named 'Ovaljaws' which is characterized by the combination of an upright growth habit, compact size, dark green foliage with an abundance of spines, and the stability of all characteristics from generation to generation. The new variety is an *Aloe*, typically produced as an indoor ornamental plant.

2 Drawing Sheets

Latin name of the genus and species: The Latin name of the genus and species of the novel variety disclosed herein is *Aloe melanacantha* A. Berger.

Variety denomination: The inventive variety of *Aloe* disclosed herein has been given the variety denomination 'Ovaljaws'.

CROSS REFERENCE TO RELATED APPLICATIONS

This application claims priority to the Community Plant Variety Rights application number 2014/3484, filed Dec. 18, 2014, which is herein incorporated by reference.

BACKGROUND OF THE INVENTION

Parentage: The *Aloe* variety 'Ovaljaws' originated as a naturally occurring, partial-plant mutation of the species *Aloe melanacantha* (not a named variety or cultivar, not patented). The inventor of 'Ovaljaws' is a commercial ornamental plant producer whom regularly discovers basal shoot mutations of the species *Aloe melanacantha* at his greenhouse operation in Bleiswijk, The Netherlands. For said mutations which seem to exhibit commercial potential, cuttings are taken to produce trial plants which are subsequently grown for evaluation. Several of such mutations were isolated for evaluation based on darker green coloration of the leaf in combination with other desirable characteristics such as compactness of the plant, upright growth habit, shorter leaves and an abundance of foliar spines. The combination of compactness and upright growth habit results in plants which require less greenhouse bench space for production, less space for shipping and a reduced risk of leaf spines coming into contact with the grower or consumer.

The variety now called 'Ovaljaws' was initially discovered in 2011 as one such mutation of the parent plant. At the time of discovery, cuttings were taken and the resulting plants were evaluated at the inventor's greenhouse. After further evaluation it was determined that the candidate's dark green foliage, compact size, upright growth habit, shorter leaves and abundance of white foliar spines would prove favorable for commercial marketability.

Asexual Reproduction: 'Ovaljaws' was first asexually propagated by leaf tip cuttings in October of 2011 at a greenhouse in Bleiswijk, The Netherlands and has since been vegetatively propagated and mericloned through seven additional generation. Through subsequent generations, the unique features of this cultivar are stable and reproduced true to type.

SUMMARY OF THE INVENTION

The cultivar 'Ovaljaws' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'Ovaljaws'. These characteristics in combination distinguish 'Ovaljaws' as a new and distinct *Aloe* cultivar:

1. *Aloe* 'Ovaljaws' exhibits dark green foliage; and
2. 'Ovaljaws' exhibits an upright growth habit; and
3. 'Ovaljaws' exhibits short leaves and a compact size; and
4. 'Ovaljaws' exhibits an abundance of white foliar spines.

BOTANICAL DESCRIPTION OF THE PLANT

Figure 1:
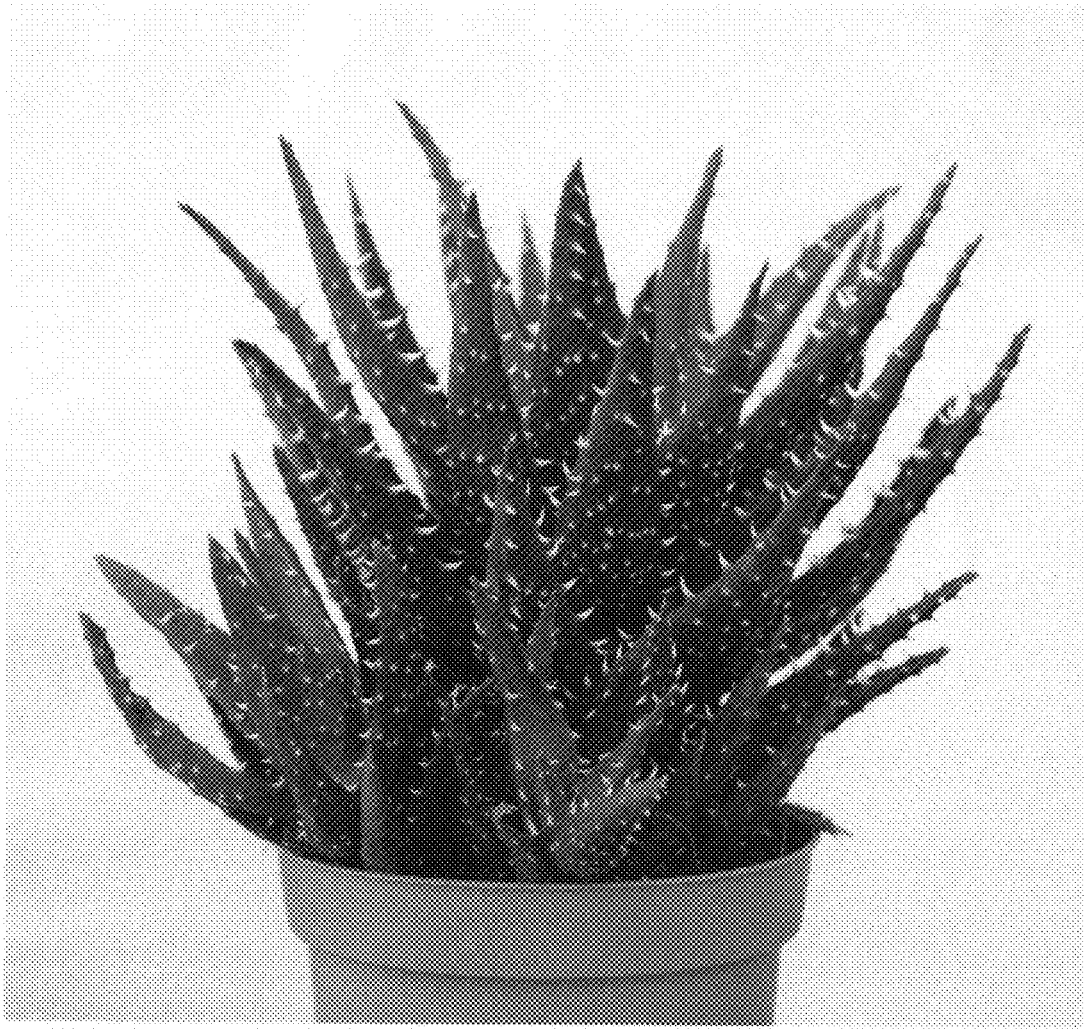
FIG. 1 illustrates, as nearly true as it is reasonably possible to make the same in color photographs of this type, an exemplary plant of 'Ovaljaws' grown in a commercial greenhouse in Bleiswijk, The Netherlands. This plant is approximately 12 months old, shown planted in a 12 cm container.
Figure 2:
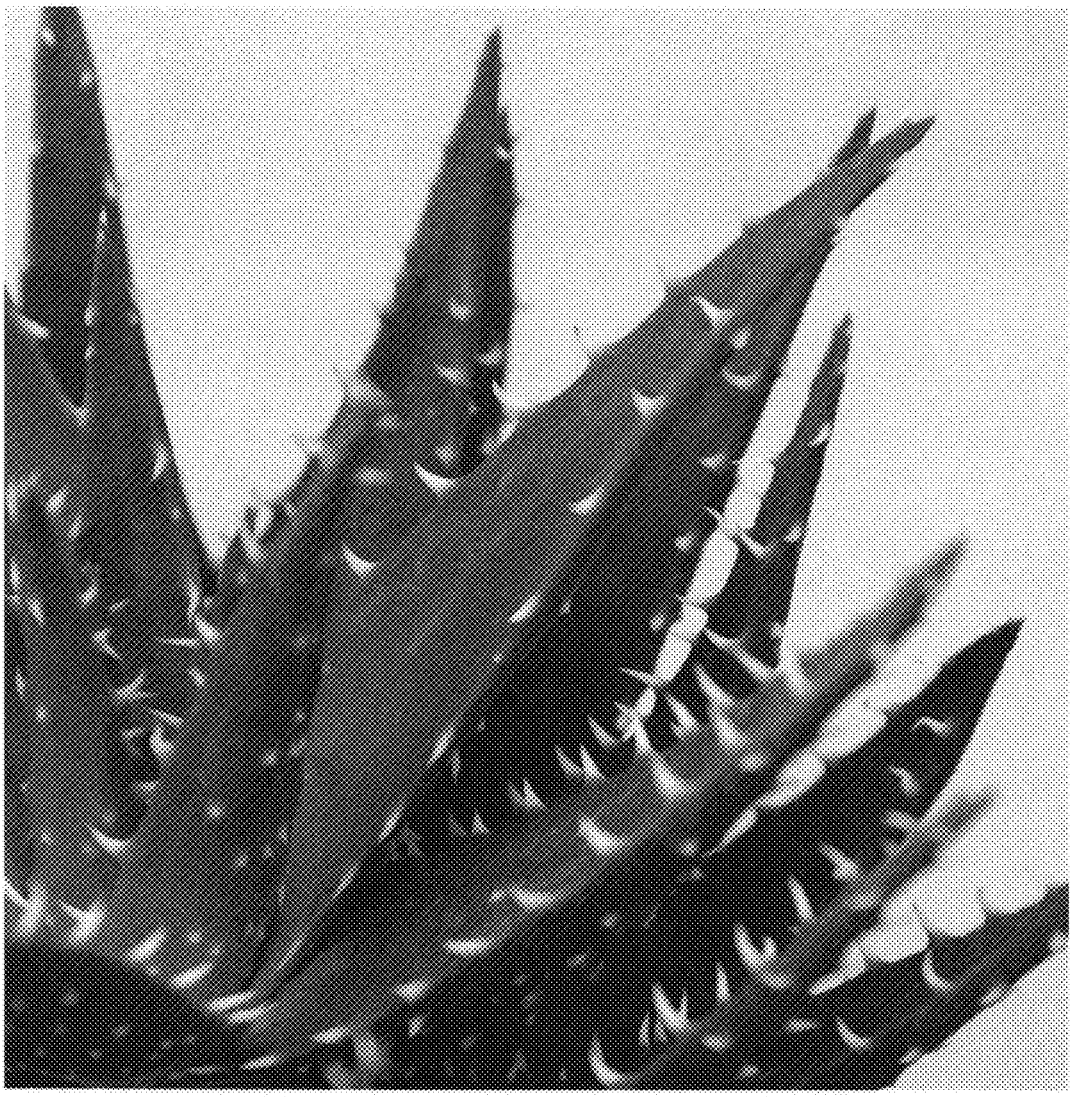
FIG. 2 illustrates, as nearly true as it is reasonably possible to make the same in color photographs of this type, the typical foliage of 'Ovaljaws'.

The following observations and measurements describe a twelve month-old 'Ovaljaws' plant grown in 12 cm nursery pots at a commercial greenhouse in Bleiswijk, The Netherlands. The plants were grown in full sun to semi-shade. Plants were maintained with a standard fertility program for plants of this type and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'Ovaljaws' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'Ovaljaws' and comparisons with other varieties of *Aloe* are provided below.

Plant description:

- *Growth habit*.—Broad and upright; overall shape is globular to broad oblong.
- *Average height*.—16.5 cm, from the soil level to the highest leaf.
- *Plant spread*.—Average of 19.6 cm.
- *Growth rate*.—Moderate; approximately 2 cm per month.
- *Propagation type*.—Vegetative cuttings and mericloning.
- *Time to initiate roots*.—Approximately 3 weeks to initiate roots at temperatures ranging from 15 to 30 degrees Celsius.
- *Time to produce a rooted cutting*.—Approximately 6 weeks to produce a rooted cutting.
- *Disease and pest resistance or susceptibility*.—Neither susceptibility nor resistance to typical *Aloe melanacantha* pests and diseases has been observed.
- *Temperature tolerances*.—Tolerates temperatures ranging from approximately 12 to 45 degrees Celsius.

Root system:

- *General*.—Thick; not fibrous.
- *Texture*.—Slightly fleshy.
- *Color*.—Greyed-red, near RHS 178A to 178B.

Foliage:

- *Arrangement*.—Basal rosette. New rosettes are formed at the base of the main rosette, approximately 2 per plant. No stems or lateral branches, the leaves form a stem-like structure not consisting of a stem as such, but only consisting of the leaf sheaths.
- *Abundance; density*.—Approximately 41 leaves per plant.
- *Lamina*.—Dimensions — 11.4 cm long (excluding the leaf sheath) and 3.6 cm wide. Thickness — Approximately 0.9 cm. Shape of blade — Lanceolate; slightly carinate. Aspec — Leaves held at an angle of approximately 65 degrees from horizontal; moderately incurved. Apex — Acuminate. Base — Sheathing. Margin — Spined; approximately 80 to 120 spines per mature leaf. Texture of adaxial surface — Glabrous, moderately glossy; moderately covered with papillae, irregularly arranged, each approximately 1.0 mm high and 1.0 mm in diameter. Texture of abaxial surface — Glabrous, slightly glossy; sparsely to moderately covered with soft spines of average length of 1.5 mm and colored white, near RHS NN155D; moderately covered with papillae, irregularly arranged in axial rows, each papilla approximately 1.0 mm high and 1.0 mm in diameter. Color — Juvenile foliage, adaxial surface — Green near RHS 137C. Juvenile foliage, abaxial surface — Green near RHS 137C; spines along the leaf margin are yellow-green, near RHS 145C. Mature foliage, adaxial surface — Green near RHS NN137A; papillae are green, nearest to RHS 138D. Mature foliage, abaxial surface — Green, in between near RHS 137A and NN137A; spines along the leaf margin are lighter, near RHS 138C to 138D; papillae are green, nearest to RHS 138D. Venation — No veins are visible.
- *Sheath*.—Sheath length — Average 2.1 cm. Sheath width — Average 4.0 cm. Sheath color — Adaxial surface is white to orange-white; in between near RHS 155B and 159D, veined greyed-purple RHS 187C. Abaxial surface is white RHS NN155A and veined greyed-yellow near RHS 160A.

Inflorescence: No flowering has been observed to date.

COMPARISONS WITH THE PARENT PLANTS

'Ovaljaws' is similar in many horticultural characteristics to its parent plant, *Aloe melanacantha*. However 'Ovaljaws' differs from its parent in the following characteristics:

1. 'Ovaljaws' exhibits a more upright growth habit when compared to *Aloe melanacantha*.
2. 'Ovaljaws' exhibits a smaller plant size when compared to *Aloe melanacantha*.
3. 'Ovaljaws' exhibits shorter leaves when compared to the leaves of *Aloe melanacantha*.
4. The foliage color of 'Ovaljaws' is dark green, whereas the foliage color of *Aloe melanacantha* is a lighter green color.
5. The foliage of 'Ovaljaws' exhibits more spines per leaf when compared to *Aloe melanacantha*.

COMPARISONS WITH THE CLOSEST KNOWN COMPARATOR

'Ovaljaws' is similar in many horticultural characteristics to the species, *Aloe mitriformis*. However 'Ovaljaws' differs from *Aloe mitriformis* in the following characteristics:

1. 'Ovaljaws' exhibits a more erect growth habit when compared to *Aloe mitriformis*.
2. 'Ovaljaws' exhibits a greater abundance of foliage when compared to *Aloe mitriformis*.

3. The foliage color of 'Ovaljaws' is dark green, whereas the foliage color of *Aloe mitriformis* is a lighter green color.
4. The foliage of 'Ovaljaws' exhibits a greater abundance of spines along the leaf margin when compared to *Aloe mitriformis.*
5. The spines along the leaf margins of 'Ovaljaws' are larger than those of *Aloe mitriformis.*
6. Spines occurring on the abaxial leaf surface of 'Ovaljaws' are more prominent than those of *Aloe mitriformis.*

That which is claimed is:

1. A new and distinct variety of *Aloe* plant named 'Ovaljaws', substantially as described and illustrated herein.

* * * * *